United States Patent [19]
Wright, Jr. et al.

[11] Patent Number: 4,568,687
[45] Date of Patent: Feb. 4, 1986

[54] N-[2-4-(1H-IMIDAZOL-1-YL)ALKYL]-ARYLAMIDES AND PHARMACEUTICAL COMPOSITIONS

[75] Inventors: William B. Wright, Jr., Woodcliff Lake, N.J.; Jeffrey B. Press, Tuxedo, N.Y.

[73] Assignee: American Cyanamid Company, Stamford, Conn.

[21] Appl. No.: 570,160

[22] Filed: Jan. 13, 1984

Related U.S. Application Data

[63] Continuation-in-part of Ser. No. 470,112, Feb. 28, 1983, abandoned.

[51] Int. Cl.$^4$ .................. A61K 31/415; C07D 233/61
[52] U.S. Cl. ..................................... 514/399; 548/341
[58] Field of Search ......................... 548/341; 514/399

[56] References Cited

PUBLICATIONS

Stuetz et al., *Chemical Abstracts*, vol. 102, (1985), No. 62,244r.
Plath et al., *Chemical Abstracts*, vol. 94, (1981), No. 15,740f.
Wright et al., *Chemical Abstracts*, vol. 102, (1985), No. 78,876j.
Jaeger et al., *Chemical Abstracts*, vol. 83, (1975), No. 114,405e.

*Primary Examiner*—Robert W. Ramsuer
*Attorney, Agent, or Firm*—Edward A. Conroy, Jr.

[57] ABSTRACT

This disclosure describes novel N-[ω-(1H-imidazol-1-yl)alkyl]arylamides which possess the property of inhibiting the enzyme thromboxane synthetase and are also useful in the treatment of hypertension and myocardial ischemia.

15 Claims, No Drawings

N-[2-4-(1H-IMIDAZOL-1-YL)ALKYL]-ARYLAMIDES AND PHARMACEUTICAL COMPOSITIONS

CROSS REFERENCE TO RELATED APPLICATION

This application is a continuation-in-part of our copending application Ser. No. 470,112, filed Feb. 28, 1983 now abandoned.

BRIEF SUMMARY OF THE INVENTION

This invention relates to new organic compounds and, more particularly, is concerned with novel N-[ω-(1H-imidazol-1-yl)alkyl]arylamides which may be represented by the following structural formula:

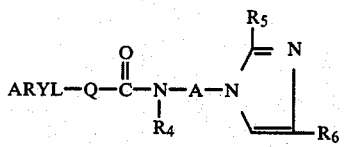

wherein A is a divalent moiety of the formulae:

$-C_nH_{2n}-$, $-CH_2CH=CHCH_2-$, $-CH_2C{\equiv}CCH_2-$ or $-\underset{\underset{C_6H_5}{|}}{CHCH_2CH_2}-$ wherein n is an integer from 2 to 8, inclusive, ARYL is 1-naphthyl, 2-naphthyl, diphenylmethyl, 9-fluorenyl or a moiety of the formula:

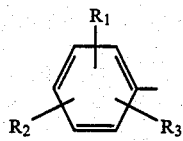

wherein $R_1$, $R_2$ and $R_3$ are each individually selected from the group consisting of hydrogen, halogen, trifluoromethyl, cyano, carboxy, amino, alkyl having from one to four carbon atoms, alkoxy having from one to four carbon atoms, benzylamino, allylamino, alkylamino having from one to three carbon atoms, dialkylamino having from one to three carbon atoms in each alkyl group, alkythio having from one to three carbon atoms, alkylsulfonyl having from one to three carbon atoms, acetyl, acetamido, phenyl and benzoyl; Q is a divalent moiety of the formulae:

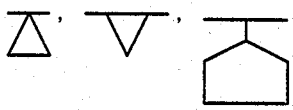

$-CH=CH-$, $-O-CH_2-$, $-\overset{\overset{O}{\|}}{C}-$ or $-C_mH_{2m}-$ wherein m is zero, 1, 2 or 3; $R_4$ is hydrogen, alkyl having from one to three carbon atoms or benzyl; and $R_5$ and $R_6$ are each individually selected from the group consisting of hydrogen, phenyl and alkyl having from one to three carbon atoms. A preferred embodiment of the present invention may be represented by the following structural formula:

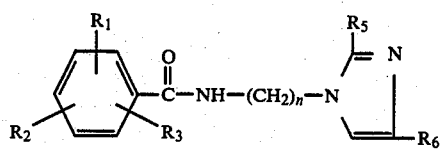

wherein $R_1$, $R_2$, $R_3$, n, $R_5$ and $R_6$ are as hereinabove defined.

The organic bases of this invention form non-toxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, maleic, sulfamic, citric, lactic, malic, succinic, tartaric, acetic, benzoic, fumaric, gluconic, ascorbic, and the like. For purposes of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

DETAILED DESCRIPTION OF THE INVENTION

The novel compounds of the present invention may be readily prepared as set forth in the following reaction schemes wherein ARYL, Q, $R_4$, A, $R_5$ and $R_6$ are as hereinabove defined; $R_7$ is hydrogen, alkyl having from one to 3 carbon atoms, allyl or benzyl; $R_8$ is benzyl or alkyl having from one to three carbon atoms; and X is chloro, bromo or moiety of the formula:

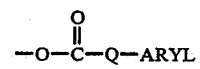

wherein ARYL and Q are as hereinabove defined and the resulting anhydride is symmetrical.

Method I

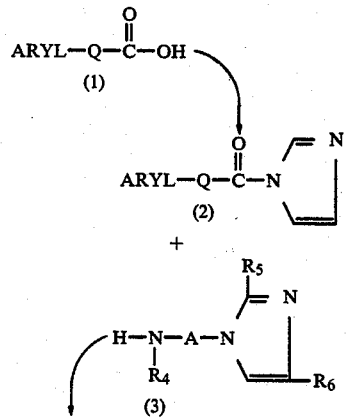

Method I

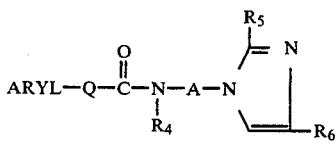

In accordance with Method I, an appropriately substituted acid (I) is reacted with 1,1'-carbonyldiimidazole in an inert solvent such as dioxane, dimethylformamide or tetrahydrofuran at ambient temperatures for 1-3 hours to provide the intermediates (2). Treatment of the intermediates (2) with an appropriately substituted 1H-imidazole-1-alkanamine (3), either as the free base or a salt thereof, provides the final products (4). The final condensation of (2)+(3) is best carried out by merely adding (3) to the reaction mixture for 1-5 hours. Concentration of the reaction mixture followed by the addition of aqueous base (KOH or NaOH) in a solvent such as $CHCl_3$ or $CCl_4$ and isolation from the organic phase provides the products (4) as the free bases.

Method II

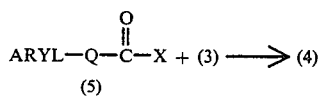

In accordance with Method II, an appropriately substituted acid halide or acid anhydride (5) is condensed with an appropriately substituted 1H-imidazole-1-alkanamine (3), either as the free base or a salt thereof, to provide the final products (4). This condensation is best carried out at ambient temperatures for up to 18 hours in an inert solvent such as $CH_2Cl_2$, $CHCl_3$ or $CCl_4$ and in the presence of an acid acceptor such as aqueous base (2N KOH or 2N NaOH), soda ash or concentrated (12%) aqueous ammonia. The resulting organic phase is then washed with water, dried, and concentrated to give the crystalline products (4) as the free bases.

Method III

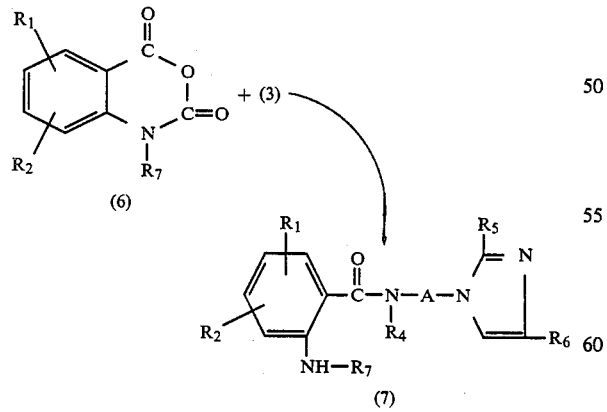

In accordance with Method III, an appropriately substituted isatoic anhydride (6) is condensed with an appropriately substituted 1H-imidazole-1-alkanamine (3) to provide the corresponding substituted 2-amino-N-[ω-(1H-imidazol-1-yl)alkyl]benzamides (7). This condensation is readily carried out in an inert solvent such as benzene, toluene, ethanol or dimethylsulfoxide at the reflux temperature thereof for a period of 15 minutes to an hour or so. The product (7) precipitates from the reaction mixture and is collected by filtration and purified.

Method IV

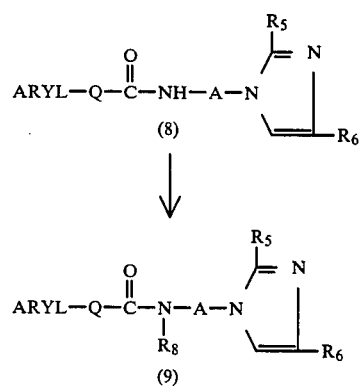

In accordance with Method IV, an appropriately substituted N-[ω-(1H-imidazol-1-yl)alkyl]arylamide (8) is treated with sodium hydride in an inert solvent such as dioxane, dimethylformamide or tetrahydrofuran at ambient temperatures for 1-3 hours to form the intermediate sodium salt in situ. Addition to the reaction mixture of an alkyl halide of the formula: $R_8$—Hal (wherein Hal is chloro, bromo or iodo), followed by stirring at ambient temperatures for 12-24 hours provides the alkylated derivative (9). Isolation of (9) is readily accomplished by concentration of the reaction mixture, dilution with water, and extraction into a water insoluble solvent such as $CH_2Cl_2$, $CHCl_3$ or $CCl_4$.

Method V

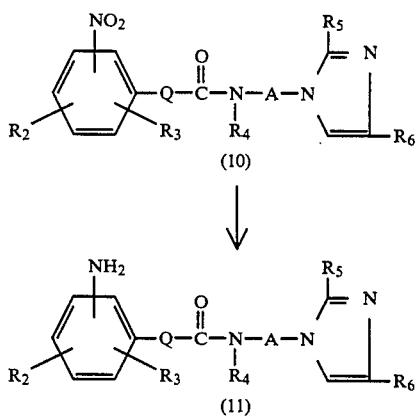

In accordance with Method V, an appropriately substituted nitro-N-[ω-(1H-imidazol-1-yl)alkyl]arylamide (10) is reduced by catalytic hydrogenation to the corresponding amino derivative (11) in a Parr apparatus at a few atmospheres pressure of hydrogen in the presence of a catalyst such as Raney nickel, palladium or carbon, and the like.

Method VI

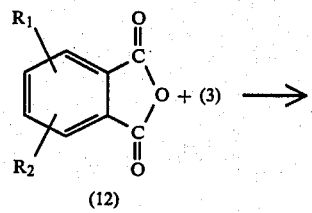

(12)

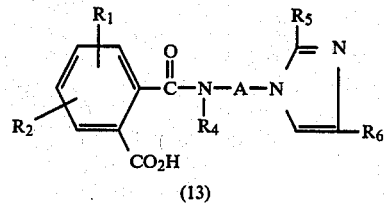

(13)

In accordance with Method VI, an appropriately substituted phthalic anhydride (12) is condensed with an appropriately substituted 1H-imidazole-1-alkanamine (3) to provide the corresponding substituted 2-carboxy-N-[ω-(1H-imidazol-1-yl)alkyl]benzamides (13). This condensation is readily carried out in an inert solvent such as methylene chloride or chloroform at room temperature for a few hours.

This invention also pertains to novel substituted N-[ω-(1H-imidazol-1-yl)alkyl]phthalimides which may be represented by the following structural formula:

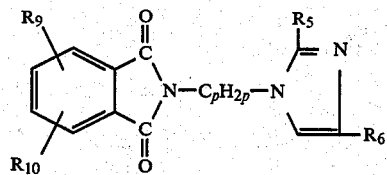

wherein p is an integer from three to ten, inclusive, $R_5$ and $R_6$ are as hereinbefore defined, and $R_9$ and $R_{10}$ are each individually selected from the group consisting of hydrogen, halogen, alkyl having from one to three carbon atoms, nitro and amino with the proviso that $R_9$ and $R_{10}$ may not both be hydrogen when p is three. These phthlaimide derivatives are intermediates for the preparation of the 1H-imidazole-1-alkanamines (3) wherein $R_4$ is hydrogen. They also possess the property of inhibiting the enzyme thromboxane synthetase and are also useful in the treatment of hypertension. These novel phthalimide derivatives may be readily prepared as set forth in the following reaction schemes wherein p, $R_5$, $R_6$, $R_9$ and $R_{10}$ are as hereinbefore defined and X is chloro, bromo or iodo.

Method A

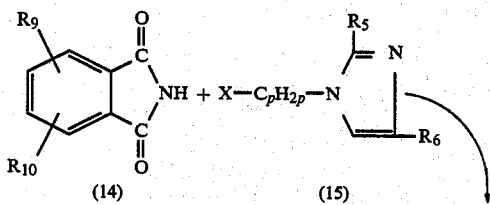

-continued
Method A

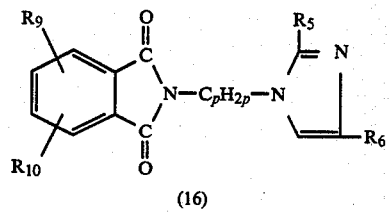

(16)

In accordance with Method A, an appropriately substituted phthalimide (14) (as the potassium salt) is condensed with an appropriately substituted N-haloalkylimidazole (15) to provide the final products (16). This condensation is best carried out in an inert solvent such as dioxane, dimethylformamide or tetrahydrofuran at 30°–100° C. for up to 18 hours.

Method B

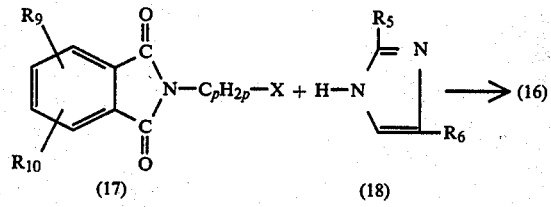

In accordance with Method B, the appropriately substituted imidazole (18) is first converted to a salt form with silver nitrate, sodium hydride, and the like and then condensed with an appropriately substituted N-haloalkylphthalimide (17) to provide the products (16). The salt formation and subsequent condensation are best carried out in an inert solvent such as dimethylformamide or methylethyl ketone at 30°–100° C. for up to 18 hours.

Method C

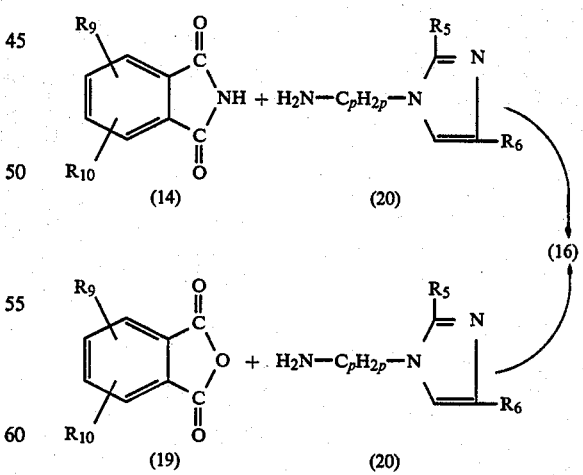

In accordance with Method C, an appropriately substituted phthalimide (14) or phthalic anhydride (19) is condensed with an appropriately substituted N-aminoalkylimidazole (20) to provide the products (16). Although this condensation may be carried out in a high boiling inert solvent at 140°–180° C. for several hours, it is most conveniently carried out neat as a simple fusion reaction.

The compounds of this invention inhibit thromboxane synthetase enzyme without interfering with other enzymes in the arachadonic acid cascade. Thus, these compounds are useful in the treatment of diseases characterized by an imbalance of thromboxane $A_2$/prostacyclin such as ischemic heart disease, transient ischemic attack, thrombosis and migraine. Recent reviews have established the role of the thromboxane/prostacyclin balance in the vascular system [*Cardiovascular Diseases: New Trends in Surgical and Medical Aspects,* H. Barnett, P. Paoletti, E. Flamm and G. Brambilla, eds., Elsevier/North-Holland Biomedical Press, pp 137–150 (1981)]. Prostacyclin ($PGI_2$) is a potent vasodilator and platelet aggregation inhibitor, whereas thromboxane ($TWA_2$) is a powerful vasoconstrictor and causative of platelet aggregation. $TXA_2$ is synthesized by thromboxane synthetase enzyme located in, for example, blood platelets. When $TXA_2$ production is increased relative to $PGI_2$, platelet aggregation, thrombosis and vasopasm may occur [*Lancet* (i), 1216 (1977); *Lancet,* 479 (1977); *Science,* 1135 (1976); *Amer. J. Cardiology,* 41, 787 (1978)]. $TXA_2$ synthetase inhibitors have been shown to have superior anti-thrombotic action to that of aspirin [*J. Clin. Invest.,* 65, 400 (1980); *Br. J. Pharmac.,* 76, 3 (1982)].

The role of prostaglandins including $TXA_2$ and $PGI_2$ in ischemic heart patients has been reviewed [*Cardiovascular Pharmacology of the Prostaglandins,* A. G. Herman, P. M. Vanhoute, H. Denolin and A. Goosens, eds., Raven Press, New York, pp 361–374 (1982)]. Injection of $TXA_2$ into coronary arteries of guinea pigs and rabbits causes myocardial ischemia and subendocardial necrosis [*Drugs of the Future,* 7, 331 (1982); *Proc. Jap. Acad.,* 53(B), 38 (1977); *Eur. J. Pharmacol.,* 53 49(1978)]. Recent research has demonstrated the beneficial effects of $PGI_2$ and selective inhibition of thromboxane synthetase on ischemic myocardium in canines [*J. Cardiovascular Pharmacology,* 4, 129 (1982)]. Thus compounds which selectively inhibit thromboxane synthetase (and hence $TXA_2$) without adversely affecting $PGI_2$ are useful in the treatment of vascular diseases such as ischemia and migraine. In addition, inhibition of $TXA_2$ formation may effectively treat platelet aggregation and prevent thrombosis.

Under urethan anesthesia, 10 μl of arterial blood was collected in one ml. of 3.2% sodium citrate in a polystyrene tube from Okamoto-Aoki spontaneously hypertensive rats (SHR) (Taconic Farms, Germantown, NY) between 19 and 24 weeks in age. The blood was diluted with 3 ml. cold saline and centrifuged at room temperature for 15 minutes at 460×g. The platelet rich plasma (PRP) was separated. The platelets were isolated by centrifuging the PRP for 10 minutes at 1060×g and were washed in 4 ml. cold oxygenated Krebs phosphate buffer, pH 7.4. The chilled patelets recovered from centrifuging at 800×g for 10 minutes were resuspended in oxygenated Krebs phosphate buffer and diluted to contain $4.5$–$6.0 \times 10^4$ platelets/μl.

The inhibition of thromboxane (TX) formation was studied by determining the condensation of thromboxane $B_2$ ($TXB_2$), the stable hydrolysis product of $TXA_2$. Assay samples, prepared on ice, contained 200 μl platelet suspension, 50 μl saline, and 50 μl vehicle or drug under study (OKY-1581, UK-37248-01, 1-benzylimidazole, or indomethacin). The samples were incubated for 10 minutes at 37° C. in a metabolic shaker. The reaction was terminated by immersing the tubes in an ice bath and adding 50 μl of 0.5M citric acid. The samples were centrifuged for 10 minutes in a refrigerated centrifuge and the supernatants thus obtained were decanted and stored at −20° C. The $TXB_2$ content for each sample was determined by a direct radioimmunoassay (RIA) utilizing a $TXB_2$ specific RIA kit purchased from New England Nuclear, Boston, MA and expressed as pg $TXB_2$ formed minute$^{-1}$ sample$^{-1}$, from which the percent inhibition of $TXB_2$ formation was calculated. The results of this test on representative compounds of this invention appear in Table I below.

TABLE I

| Product | Dose | % Inhibition |
|---|---|---|
| 3,4-dichloro-N—[3-(1H—imidazol-1-yl)-propyl]benzamide | $10^{-4}$ | 92.7 |
| 3,4-dichloro-N—[2-(1H—imidazol-1-yl)-ethyl]benzamide | $10^{-4}$ | 58.5 |
| 4-fluoro-N—[3-(1H—imidazol-1-yl)-propyl]benzamide | $10^{-4}$ | 87.1 |
| N—[3-(1H—imidazol-1-yl)propyl]benzamide | $10^{-4}$ | 96.3 |
| 3-trifluoromethyl-N—[3-(1H—imidazol-1-yl)propyl]benzamide | $10^{-4}$ | 84 |
| N—[3-(1H—imidazol-1-yl)propyl]-9H—fluorene-9-carboxamide | $10^{-4}$ | 100 |
| N—[3-(1H—imidazol-1-yl)propyl]-2-naphthalenecarboxamide | $10^{-4}$ | 97 |
| 2-chloro-N—[3-(1H—imidazol-1-yl)-propyl]benzamide | $10^{-4}$ | 99.7 |
| 2-fluoro-N—[3-(1H—imidazol-1-yl)-propyl]benzamide | $10^{-4}$ | 83.9 |
| 4-chloro-N—[3-(1H—imidazol-1-yl)-propyl]benzamide | $10^{-4}$ | 95 |
| 3-chloro-N—[3-(1H—imidazol-1-yl)-propyl]benzamide | $10^{-4}$ | 75.4 |
| 3-fluoro-N—[3-(1H—imidazol-1-yl)-propyl]benzamide | $10^{-4}$ | 95.8 |
| N—[3-(1H—imidazol-1-yl)propyl]-4-methylbenzamide | $10^{-4}$ | 83.2 |
| 4-bromo-N—[3-(1H—imidazol-1-yl)-propyl]benzamide | $10^{-4}$ | 85 |
| 4-acetyl-N—[3-(1H—imidazol-1-yl)-propyl]benzamide | $10^{-4}$ | 89.5 |
| 4-fluoro-N—[3-(1H—imidazol-1-yl)-propyl]benzeneacetamide, fumarate | $10^{-4}$ | 53.1 |
| N—[3-(1H—imidazol-1-yl)propyl]-α-oxo benzeneacetamide, fumarate | $10^{-4}$ | 79.7 |
| N—[3-(1H—imidazol-1-yl)propyl]-2-phenoxyacetamide | $10^{-4}$ | 86.2 |
| 4-benzoyl-N—[3-(1H—imidazol-1-yl)-propyl]benzamide | $10^{-4}$ | 103.4 |
| N—[3-(1H—imidazol-1-yl)propyl]-1-naphthalenecarboxamide | $10^{-4}$ | 75 |
| 4-chloro-N—[3-(4-phenyl-1H—imidazol-1-yl)propyl]benzamide | $10^{-4}$ | 69 |
| N—[3-(1H—imidazol-1-yl)propyl][1,1'-biphenyl]-4-carboxamide | $10^{-4}$ | 105.7 |
| N—[3-(1H—imidazol-1-yl)propyl]-3,4,5-trimethoxybenzamide | $10^{-4}$ | 100.9 |
| 4-(acetylamino)-N—[3-(1H—imidazol-1-yl)propyl]benzamide | $10^{-4}$ | 98.7 |
| 2-(4-chlorophenoxy)-N—[3-(1H—imidazol-1-yl)propyl]acetamide | $10^{-4}$ | 84.6 |
| N—[3-(1H—imidazol-1-yl)propyl]-4-methoxybenzamide | $10^{-4}$ | 88.9 |
| N—[3-(1H—imidazol-1-yl)propyl]-4-iodobenzamide | $10^{-4}$ | 96.7 |
| 4-cyano-N—[3-(1H—imidazol-1-yl)-propyl]benzamide | $10^{-4}$ | 90.7 |
| N—[3-(1H—imidazol-1-yl)propyl]-4-(methylthio)-benzamide | $10^{-4}$ | 101.8 |
| N—[3-(1H—imidazol-1-yl)propyl]-4-(methylsulfonyl)-benzamide | $10^{-4}$ | 80.1 |
| 3,4-dichloro-N—[4-(1H—imidazol-1-yl)-butyl]benzamide | $10^{-4}$ | 100 |
| N—[3-(1H—imidazol-1-yl)propyl]-4-(dimethylamino)benzamide | $10^{-4}$ | 93 |
| 2-(2,3-dichlorophenoxy)-N—[3-(1H—imidazol-1-yl)propyl]acetamide, fumarate | $10^{-4}$ | 100 |

TABLE I-continued

| Product | Dose | % Inhibition |
|---|---|---|
| 4-bromo-N—[3-(4-phenyl-1H—imidazol-1-yl)propyl]benzamide | $10^{-4}$ | 66 |
| 3-chloro-N—[3-(4-methyl-1H—imidazol-1-yl)propyl]benzamide | $10^{-4}$ | 84 |
| 4-chloro-N—[3-4-methyl-1H—imidazol-1-yl)propyl]benzamide | $10^{-4}$ | 93 |
| 3-bromo-N—[3-(4-methyl-1H—imidazol-1-yl)propyl]benzamide | $10^{-4}$ | 93 |
| 4-bromo-N—[3-(4-methyl-1H—imidazol-1-yl)propyl]benzamide | $10^{-4}$ | 80 |
| 4-iodo-N—[3-(4-methyl-1H—imidazol-1-yl)propyl]benzamide | $10^{-4}$ | 99 |
| 3,4-dichloro-N—[3-(4-methyl-1H—imidazol-1-yl)propyl]benzamide | $10^{-4}$ | 90 |
| 4-trifluoromethyl-N—[3-(4-methyl-1H—imidazol-1-yl)propyl]benzamide | $10^{-4}$ | 92 |
| 4-methyl-N—[3-(4-methyl-1H—imidazol-1-yl)propyl]phenylacetamide | $10^{-4}$ | 76 |
| 4-trifluoromethyl-N—[4-(1H—imidazol-1-yl)butyl]benzamide fumarate | $10^{-4}$ | 97 |
| N—[4-(1H—imidazol-1-yl)butyl]-1-naphthalenecarboxamide | $10^{-4}$ | 95 |
| 2-phenyl-N—[3-(1H—imidazol-1-yl)propyl]benzamide | $10^{-4}$ | 95 |
| N—[3-(1H—imidazol-1-yl)propyl]diphenylacetamide | $10^{-4}$ | 84 |
| 2-amino-5-chloro-N—[3-(1H—imidazol-1-yl)-propyl]benzamide | $10^{-4}$ | 96 |
| 2-allylamino-5-chloro-N—[3-(1H—imidazol-1-yl)propyl]benzamide | $10^{-4}$ | 95 |
| 2-amino-5-chloro-3-methyl-N—[3-(1H—imidazol-1-yl)propyl]benzamide dihydrochloride | $10^{-4}$ | 80 |
| 2-methylamino-N—[3-(1H—imidazol-1-yl)-propyl]benzamide | $10^{-4}$ | 57 |
| 2-[4-(1H—imidazol-1-yl)butyl]-1H—isoindole-1,3(2H)—dione | $10^{-4}$ | 99 |
| 2-[5-(1H—imidazol-1-yl)pentyl]-1H—isoindole-1,3(2H)—dione | $10^{-4}$ | 92 |
| 2-ethylamino-N—[3-(1H—imidazol-1-yl)propyl]benzamide | $10^{-4}$ | 86 |
| 4-chloro-N—[3-(1H—imidazol-1-yl)-2-methylpropyl]benzamide fumarate | $10^{-4}$ | 100 |
| 3-chloro-N—[3-(1H—imidazol-1-yl)-butyl]benzamide | $10^{-4}$ | 93 |
| 3,4-dichloro-N—[3-(1H—imidazol-1-yl)butyl]benzamide | $10^{-4}$ | 86 |
| 4-bromo-N—[3-(1H—imidazol-1-yl)butyl]benzamide | $10^{-4}$ | 91 |
| 4-chloro-N—[3-(1H—imidazol-1-yl)butyl]benzamide | $10^{-4}$ | 96 |
| 4-chloro-N—[3-(1H—imidazol-1-yl)-1-phenylpropyl]benzamide | $10^{-4}$ | 100 |
| 4-bromo-N—[3-(1H—imidazol-1-yl)-1-phenylpropyl]benzamide | $10^{-4}$ | 100 |

The novel compounds of the present invention are also active hypotensive agents and were tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain, from Taconic Farms, Germantown, N.Y. having an average mean arterial blood pressure of 160±1.5 mm of mercury are used in the test. One to 3 rats are used per test compound. A rat is dosed by gavage with a test compound, suspended in 2% pre-boiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading is given 24 hours later. At 28 hours after the initial dose, the mean arterial blood pressure (MABP) is measured by the method of Chan and Poorvin vide supra. The procedure is repeated in a second and third rat when necessary. Based on the data obtained and using the three-stage "sequential probability ratio test" statistical method, the criteria for activity or retest are as follows:

If the blood pressure in the first rat is $\leq 116$ mm mercury the compound is considered active. If the blood pressure is between 117 and 146 mm, a second rat is used. If the average blood pressure of the first and second rats is $\leq 122$ mm the compound is considered active. If the average blood pressure is between 123 and 137 mm, a third rat is used. If the average blood pressure of the three rats is $\leq 128$ mm the compound is considered active. The results of this test on representative compounds of the present invention appear in Table II below.

TABLE II

| Compound | MABP/mm Hg (no. of rats) |
|---|---|
| N—[3-(1H—imidazol-1-yl)propyl]benzamide | 128 (3) |
| 4-chloro-N—[3-(1H—imidazol-1-yl)propyl]-benzamide | 126 (3) |
| 3-chloro-N—[3-(1H—imidazol-1-yl)propyl]-benzamide | 124 (3) |
| 4-bromo-N—[3-(1H—imidazol-1-yl)propyl]-benzamide | 120 (3) |
| 4-bromo-N—[3-(4-methyl-1H—imidazol-1-yl)-propyl]benzamide | 122 (3) |
| 3,4-dichloro-N—[3-(4-methyl-1H—imidazol-1-yl)propyl]benzamide | 116 (2) |
| N—[3-(1H—imidazol-1-yl)propyl]-4-methyl-benzeneacetamide, hemifumarate | 109 (2) |
| 4-bromo-N—[3-(2-phenyl-1H—imidazol-1-yl)-propyl]benzamide, fumarate | 115 (2) |
| N—[3-(1H—imidazol-1-yl)propyl]-2-naphthalenecarboxamide | 127 (4) |
| N—[3-(1H—imidazol-1-yl)propyl]-1-naphthalenecarboxamide | 124 (3) |
| 4-chloro-N—[3-(4-phenyl-1H—imidazol-1-yl)-propyl]benzamide | 125 (3) |
| 4-chloro-N—[3-(2-methyl-1H—imidazol-1-yl)-propyl]benzamide | 121 (2) |
| 2-[4-(1H—imidazol-1-yl)butyl]-1H—isoindole-1,3(2H)—dione | 120 (2) |
| 2-[6-(1H—imidazol-1-yl)hexyl]-1H—isoindole-1,3(2H)—dione | 110 (1) |
| 2-[3-(1H—imidazol-1-yl)butyl]-1H—isoindole-1,3(2H)—dione | 124 (3) |
| 3-chloro-N—[3-(4-methyl-1H—imidazol-1-yl)propyl]benzamide | 122 (3) |
| 4-chloro-N—[3-(4-methyl-1H—imidazol-1-yl)propyl]benzamide | 112 (2) |
| 3,4-dichloro-N—[3-(4-methyl-1H—imidazol-1-yl)propyl]benzamide | 116 (2) |
| 4-trifluoromethyl-N—[3-(4-methyl-1H—imidazol-1-yl)propyl]benzamide | 114 (2) |
| 4-trifluoromethyl-N—[4-1H—imidazol-1-yl)butyl]benzamide fumarate | 123 (3) |
| 2-phenyl-N—[3-(1H—imidazol-1-yl)propyl]-benzamide | 124 (3) |
| 2-amino-5-chloro-N—[3-(1H—imidazol-1-yl)propyl]benzamide | 113 (1) |
| 2-allylamino-5-chloro-N—[3-(1H—imidazol-1-yl)propyl]benzamide | 124 (3) |
| 2-amino-5-chloro-3-methyl-N—[3-(1H—imidazol-1-yl)propyl]benzamide dihydrochloride | 125 (3) |
| 3,4-dichoro-N—[3-(1H—imidazol-1-yl)-butyl]benzamide | 123 (3) |

The novel compounds of the present invention have been found to be highly useful for inhibiting thromboxane synthetase in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 35 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weight of from about 200 to 1500. Although the amount of active compound dissolved in the above vehicle may vary from 0.10% to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1

3-Chloro-N-[3-(1H-imidazol-1-yl)propyl]benzamide

A mixture of 6.0 g. of 1H-imidazole-1-propanamine dihydrochloride, 45 ml. of 2N sodium hydroxide and 150 ml. of methylene chloride was stirred at room temperature and 3.9 ml. of 3-chlorobenzoyl chloride was added. The reaction mixture was stirred for 18 hours, then methylene chloride and 15 ml. of 1N sodium hydroxide were added and the layers were separated. The organic layer was washed with water, dried over magnesium sulfate, and concentrated to remove the solvent. The residue was triturated with diethyl ether and the crystalline product recovered by filtration and recrystallized from ethanol, giving the desired product, m.p. 125°–127° C.

Following the procedure of this example and using the appropriate benzoyl chloride, the products of Examples 2–19 were obtained as set forth in Table III below.

TABLE III

| Ex. | Benzoyl Chloride | Product | m.p.°C. |
|---|---|---|---|
| 2 | 2-chlorobenzoyl chloride | 2-chloro-N—[3-(1H—imidazol-1-yl)propyl]benzamide | 98–101 |
| 3 | 4-chlorobenzoyl chloride | 4-chloro-N—[3-(1H—imidazol-1-yl)propyl]benzamide | 141–143 |
| 4 | 3,4-dichlorobenzoyl chloride | 3,4-dichloro-N—[3-(1H—imidazol-1-yl)propyl]benzamide | 158–160 |
| 5 | 2-fluorobenzoyl chloride | 2-fluoro-N—[3-(1H—imidazol-1-yl)propyl]benzamide | 73–75 |
| 6 | 3-fluorobenzoyl chloride | 3-fluoro-N—[3-(1H—imidazol-1-yl)propyl]benzamide | 136—138 |
| 7 | 4-fluorobenzoyl chloride | 4-fluoro-N—[3-(1H—imidazol-1-yl)propyl]benzamide | 73–75 |
| 8 | 3-bromobenzoyl chloride | 3-bromo-N—[3-(1H—imidazol-1-yl)propyl]benzamide | 113–115 |
| 9 | 4-bromobenzoyl chloride | 4-bromo-N—[3-(1H—imidazol-1-yl)propyl]benzamide | 156–159 |
| 10 | 4-trifluoromethylbenzoyl chloride | 4-trifluoromethyl-N—[3-(1H—imidazol-1-yl)propyl]benzamide | 107–109 |
| 11 | 4-methylbenzoyl chloride | N—[3-(1H—imidazol-1-yl)propyl]-4-methylbenzamide | 107–109 |

TABLE III-continued

| Ex. | Benzoyl Chloride | Product | m.p.°C. |
|---|---|---|---|
| 12 | 4-cyanobenzoyl chloride | 4-cyano-N—[3-(1H—imidazol-1-yl)propyl]benzamide | 154–156 |
| 13 | 3-nitrobenzoyl chloride | N—[3-(1H—imidazol-1-yl)propyl]-3-nitrobenzamide | 124–126 |
| 14 | 4-(1,1-dimethylethyl)benzoyl chloride | N—[3-(1H—imidazol-1-yl)propyl]-4-(1,1-dimethylethyl)benzamide | oil |
| 15 | 3-trifluoromethylbenzoyl chloride | 3-trifluoromethyl-N—[3-(1H—imidazol-1-yl)propyl]benzamide | 82–84 |
| 16 | 9-fluorenecarbonyl chloride | N—[3-(1H—imidazol-1-yl)propyl]-9H—fluorene-9-carboxamide | 164–167 |
| 17 | 2-naphthoyl chloride | N—[3-(1H—imidazol-1-yl)propyl]-2-naphthalenecarboxamide | 99–101 |
| 18 | 1-naphthoyl chloride | N—[3-(1H—imidazol-1-yl)propyl]-1-naphthalenecarboxamide | 108–110 |
| 19 | 2-phenylbenzoyl chloride | 2-phenyl-N—[3-(1H—imidazol-1-yl)propyl]benzamide | 90–92 |

Following the procedure of Example 1 and using the appropriate benzoyl chloride but substituting 1H-imidazole-1-ethanamine dihydrochloride for the 1H-imidazole-1-propanamine dihydrochloride of that example, the products of Examples 20 and 21 were obtained as set forth in Table IV below.

TABLE IV

| Ex. | Benzoyl Chloride | Product | m.p. °C. |
|---|---|---|---|
| 20 | 4-fluorobenzoyl chloride | 4-fluoro-N—[2-(1H—imidazol-1-yl)ethyl]benzamide | 121–123 |
| 21 | 3,4-dichlorobenzoyl chloride | 3,4-dichloro-N—[2-(1H—imidazol-1-yl)ethyl]benzamide | 137–140 |

When the procedure of Example 1 is carried out using 4-chlorobenzoyl chloride or 4-bromobenzoyl chloride and the appropriate imidazole derivative, the products of Examples 22–25 were obtained as set forth in Table V below.

TABLE V

| Ex. | Imidazole Derivative | Product | m.p. °C. |
|---|---|---|---|
| 22 | 2,4-dimethyl-1H—imidazole-1-propanamine dihydrochloride | 4-chloro-N—[3-(2,4-dimethyl-1H—imidazol-1-yl)propyl]benzamide | oil |
| 23 | 2-phenyl-1H—imidazole-1-propanamine dihydrochloride | 4-bromo-N—[3-(2-phenyl-1H—imidazol-1-yl)propyl]benzamide | 162–165 |
| 24 | 4-phenyl-1H—imidazole-1-propanamine | 4-chloro-N—[3-(4-phenyl-1H—imidazol-1-yl)propyl]benzamide | 119–120 |
| 25 | 4-phenyl-1H—imidazole-1-propanamine | 4-bromo-N—[3-(4-phenyl-1H—imidazol-1-yl)propyl]benzamide | 133–135 |

EXAMPLE 26

1H-Imidazole-1-propanamine Derivatives

A mixture of 16.4 g. of 4-methylimidazole and 25 ml. of acrylonitrile was heated at reflux temperature for 4 hours and then concentrated to remove the volatile material. The residue was mixed with 200 ml. of ethanol, 100 ml. of ammonium hydroxide and 6 g. of Raney Nickel catalyst and reduced in a Parr Hydrogentator under hydrogen pressure until reduction was complete. The catalyst was removed by filtration and the mother liquor was concentrated to remove the solvents. The residual oil was 4-methyl-1H-imidazole-1-propanamine. By substituting the appropriate imidazole starting material in the above procedure, the following intermediates were prepared: 2-methyl-1H-imidazole-1-propanamine, 2-ethyl-1H-imidazole-1-propanamine, 2,4-dimethyl-1H-imidazole-1-propanamine, 2-phenyl-1H-imidazole-1-propanamine and 4-phenyl-1H-imidazole-1-propanamine.

EXAMPLE 27

4-Chloro-N-[3-(2ethyl-1H-imidazol-1-yl)propyl]benzamide

A mixture of 2.3 g. of 2-ethyl-1H-imidazole-1-propanediamine, 15 ml. of 2N sodium hydroxide and 150 ml. of methylene chloride was stirred at room temperature and 4.0 ml. of 4-chlorobenzoyl chloride was added. The reaction mixture was stirred for 18 hours, then methylene chloride and 15 ml. of 1N sodium hydroxide were added and the layers were separated. The organic layer was washed with water, dried over magnesium sulfate and concentrated. The crystalline residue was washed onto a filter with ether and melted at 120°–122° C.

EXAMPLE 28

N-[3-(1H-Imidazol-1-yl)propyl]benzamide

A mixture of 1.22 g. of benzoic acid, 1.62 g. of 1,1'-carbonyldiimidazole and 30 ml. of tetrahydrofuran was stirred for 3 hours, then 1.98 g. of 1H-imidazole-1-propanamine dihydrochloride was added. The reaction mixture was stirred for 18 hours, then heated at reflux for 5 hours, then diluted with 5 ml. of water and heated for an additional 30 minutes. The mixture was concentrated to remove most of the solvent and to the residue was added chloroform and 35 ml. of 1N sodium hydroxide. The layers were separated. The organic layer was washed with water, dried over magnesium sulfate, concentrated and diethyl ether was added, giving the desired product, m.p. 134°–136° C.

Following the procedure of this example and using the appropriate benzoic acid derivative, the products of Examples 29–40 were obtained as set forth in Table VI below.

TABLE VI

| Ex. | Benzoic Acid | Product | m.p.°C. |
|---|---|---|---|
| 29 | 4-methoxybenzoic acid | N—[3-(1H—imidazol-1-yl)propyl]-4-methoxybenzamide | 132–135 |
| 30 | 3,4,5-trimethoxybenzoic acid | N—[3-(1H—imidazol-1-yl)propyl]-3,4,5-trimethoxybenzamide | 155–158 |
| 31 | 4-n-butoxybenzoic acid | 4-n-butoxy-N—[3-(1H—imidazol-1-yl)propyl]benzamide | 82–84 |
| 32 | 4-acetylbenzoic acid | 4-acetyl-N—[3-(1H—imidazol-1-yl)propyl]benzamide | 132–134 |
| 33 | 4-acetylaminobenzoic acid | 4-(acetylamino)-N—[3-(1H—imidazol-1-yl)propyl]benzamide | 230–232 |
| 34 | 4-methylthiobenzoic acid | N—[3-(1H—imidazol-1-yl)propyl]-4-(methylthio)benzamide | 132–134 |
| 35 | 4-methylsulfonylbenzoic acid | N—[3-(1H—imidazol-1-yl)propyl]-4-(methylsulfonyl)benzamide | 174–176 |
| 36 | 4-iodobenzoic acid | N—[3-(1H—imidazol-1-yl)propyl]-4- | 156–159 |

TABLE VI-continued

| Ex. | Benzoic Acid | Product | m.p.°C. |
|---|---|---|---|
| 37 | 4-phenyl-benzoic acid | N—[3-(1H—imidazol-1-yl)propyl(1.1'-biphenyl)-4-carboxamide iodobenzamide | 138–140 |
| 38 | 4-benzoyl-benzoic acid | 4-benzoyl-N—[3-(1H—imidazol-1-yl)propyl]benzamide | 107–109 |
| 39 | 4-dimethylamino-benzoic acid | N—[3-(1H—imidazol-1-yl)propyl]-4-(dimethylamino)benzamide | 133–135 |
| 40 | 2-bromobenzoic acid | N—[3-(1H—imidazol-1-yl)-propyl]-2-bromobenzamide | 95–98 |

EXAMPLES 41–45

Substituted N-[3-(2-methyl-1H-imidazol-1-yl)propyl]benzamides

By following the procedure of Example 27, the reaction of the appropriate benzoyl halide with 2-methyl-1H-imidazole-1-propanamine provides the compounds set forth in Table VII below.

TABLE VII

| Ex. | Benzoylhalide | Product | m.p.°C. |
|---|---|---|---|
| 41 | 4-chlorobenzoyl chloride | 4-chloro-N—[3-(2-methyl-1H—imidazol-1-yl)propyl]benzamide | 142–144 |
| 42 | 3-chlorobenzoyl chloride | 3-chloro-N—[3-(2-methyl-1H—imidazol-1-yl)propyl]benzamide | 130–132 |
| 43 | 4-bromobenzoyl chloride | 4-bromo-N—[3-(2-methyl-1H—imidazol-1-yl)-propyl]benzamide | 154–156 |
| 44 | 3,4-dichlorobenzoyl chloride | 3,4-dichloro-N—[3-(2-methyl-1H—imidazol-1-yl)-propyl]benzamide | 135–138 |
| 45 | 4-trifluoro-methyl benzoyl chloride | 4-trifluoromethyl-N—[3-(2-methyl-1H—imidazol-1-yl)-propyl]benzamide | 124–126 |

EXAMPLES 46–55

Substituted N-[3-(4-methyl-1H-imidazol-1-yl)propyl]amides

By following the procedure of Example 27, the reaction of the appropriate acid halide with 4-methyl-1H-imidazole-1-propanamine provides the compounds of Table VIII.

TABLE VIII

| Ex. | Acid halide | Product | m.p.°C. |
|---|---|---|---|
| 46 | 3-chlorobenzoyl chloride | 3-chloro-N—[3-(4-methyl-1H—imidazol-1-yl)propyl]benzamide | 109–111 |
| 47 | 4-chlorobenzoyl chloride | 4-chloro-N—[3-(4-methyl-1H—imidazol-1-yl)propyl]benzamide | 126–130 |
| 48 | 3-bromobenzoyl chloride | 3-bromo-N—[3-(4-methyl-1H—imidazol-1-yl)propyl]benzamide | 108–112 |
| 49 | 4-bromobenzoyl chloride | 4-bromo-N—[3-(4-methyl-1H—imidazol-1-yl)propyl]benzamide | 125–127 |
| 50 | 4-iodobenzoyl chloride | 4-iodo-N—[3-(4-methyl-1H—imidazol-1-yl)propyl]benzamide | 124–131 |
| 51 | 3,4-dichlorobenzoyl chloride | 3,4-dichoro-N—[3-(4-methyl-1H—imidazol-1-yl)propyl]benzamide | 127–132 |
| 52 | 4-trifluoromethyl-benzoyl chloride | 4-trifluoromethyl-N—[3-(4-methyl-1H—imidazol-1-yl)propyl]benzamide | 120–126 |
| 53 | 4-methylphenyl-acetyl chloride | 4-methyl-N—[3-(4-methyl-1H—imidazol-1-yl)-propyl]phenylacetamide | 89–91 |
| 54 | 2-phenylbenzoyl chloride | 2-phenyl-N—[3-(4-methyl-1H—imidazol-1-yl)-propyl]benzamide fumarate | 60 dec. |
| 55 | 1-naphthoyl chloride | N—[3-(4-methyl-1H—imidazol-1-yl)propyl]naphthalene-1-carboxamide | 110–123 |

EXAMPLE 56

2-[4-(1H-Imidazol-1-yl)butyl]-1H-isoindole-1,3(2H)-dione

A mixture of 0.2 mol. of N-(4-bromobutyl)-1H-isoindole-1,3(2H)-dione, 0.22 mol. of sodium imidazole and 300 ml. of dimethylformamide was stirred at 100° C. for 8 hours and then concentrated to remove the dimethylformamide. The residue was boiled with 500 ml. of toluene and the insoluble material was removed by filtration. The toluene layer was concentrated to remove the solvent and the residue was further purified by HPLC using ethyl acetate and a silica gel column. The desired product melted at 75°–77° C. Addition of ethanolic hydrogen chloride resulted in the hydrochloride salt, mp. 200°–203° C.

When the above procedure is used to react sodium imidazole with the appropriate 2-(ω-bromoalkyl)-1H-isoindole-1,3(2H)-dione, the compounds of Table IX were obtained.

TABLE IX

| Ex. | Product | m.p. °C. |
|---|---|---|
| 57 | 2-[5-(1H—imidazol-1-yl)pentyl]-1H—isoindole-1,3(2H)—dione hydrochloride | 194–197 |
| 58 | 2-[6-(1H—imidazol-1-yl)hexyl]-1H—isoindole-1,3(2H)—dione | 83–87 |
| 59 | 2-[7-(1H—imidazol-1-yl)heptyl]-1H—isoindole-1,3(2H)—dione | oil |
| 60 | 2-[8-(1H—imidazol-1-yl)octyl]-1H—isoindole-1,3(2H)—dione | 43–45 |
| 61 | 2-[9-(1H—imidazol-1-yl)nonyl]-1H—isoindole-1,3(2H)—dione | oil |
| 62 | 2-[10-(1H—imidazol-1-yl)decyl]-1H—isoindole-1,3(2H)—dione | 69–70 |

EXAMPLE 63

1H-Imidazole-1-butanamine

A mixture of 0.2 mole of 2-[4-(1H-imidazol-1-yl)butyl]-1H-isoindole-1,3(2H)-dione, 0.22 mol. of hydrazine hydrate and 400 ml. of ethanol was heated on the steam bath for 3 hours and then treated with 400 ml. of 3N HCl and heated at reflux for an additional 2 hours. The insoluble material was filtered off and the mother liquor was concentrated to a low volume and again filtered. The remainder of the volatile material was distilled off and the residue was treated with saturated potassium carbonate solution. The 1H-imidazole- 1-butanamine was extracted into methylene chloride and further purified by distillation on a Kugelrohr apparatus. In like manner from the appropriate 2-[ω-(1H-imidazol-1-yl)alkyl]-1H-isoindole-1,3(2H)-dione were prepared 1H-imidazole-1-pentanamine, 1H-imidazole-1-hexanamine, 1H-imidazole-1-heptanamine and 1H-imidazole-1-octanamine.

EXAMPLE 64

3,4-Dichloro-N-[4-(1H-imidazol-1-yl)butyl]benzamide

A solution of 1.05 g. of 3,4-dichlorobenzoyl chloride in 25 ml. of methylene chloride was added to a stirred solution of 1.06 g. of 1H-imidazole-1-butanamine dihydrochloride in 15 ml. of 1N sodium hydroxide. The mixture was stirred for 18 hours, methylene chloride was added and the layers were separated. The organic layer was washed with water, dried over magnesium sulfate and concentrated. The residue was washed onto a filter with diethyl ether, giving the desired product, m.p. 86°-88° C.

Following the procedure of this example and using the appropriate benzoyl chloride, the products of Examples 65-70 were obtained as set forth in Table X below.

TABLE X

| Ex. | Benzoyl Chloride | Product | m.p. °C. |
|---|---|---|---|
| 65 | 4-chlorobenzoyl chloride | 4-chloro-N—[4-(1H—imidazol-1-yl)butyl]benzamide | 70-72 |
| 66 | 4-bromobenzoyl chloride | 4-bromo-N—[4-(1H—imidazol-1-yl)butyl]benzamide | 105-106 |
| 67 | 4-iodobenzoyl chloride | 4-iodo-N—[4-(1H—imidazol-1-yl)butyl]benzamide | 153-155 |
| 68 | 4-acetylbenzoyl chloride | 4-acetyl-N—[4-(1H—imidazol-1-yl)butyl]benzamide | 70-83 |
| 69 | 4-trifluoromethylbenzoyl chloride | 4-trifluoromethyl-N—[4-(1H—imidazol-1-yl)butyl]benzamide fumarate | 103-120 |
| 70 | 1-naphthoyl chloride | N—[4-(1H—imidazol-1-yl)butyl]-naphthalene-1-carboxamide | 97-100 |

EXAMPLES 71-75

Substituted N-[w-(1H-imidazol-1-yl)alkyl]benzamides

The compounds set forth in Table XI below were prepared from the appropriate 1H-imidazole-1-alkanamine (Example 63) by reaction with 4-chlorobenzoyl chloride, 4-bromobenzoyl chloride or 4-trifluoromethylbenzoyl chloride by the procedure of Example 1 but using the base instead of the hydrochloride salt.

TABLE XI

| Ex. | Compound | m.p.°C. |
|---|---|---|
| 71 | 4-chloro-N—[5-(1H—imidazol-1-yl)pentyl]benzamide | 92-94 |
| 72 | 4-bromo-N—[5-(1H—imidazol-1-yl)pentyl]benzamide | 104-106 |
| 73 | 4-chloro-N—[6-(1H—imidazol-1-yl)hexyl]benzamide | 72-76 |
| 74 | 4-trifluoromethyl-N—[5-(1H—imidazol-1-yl)pentyl]benzamide | 76-78 |
| 75 | 4-chloro-N—[8-(1H—imidazol-1-yl)octyl]benzamide | 83-85 |

EXAMPLE 76

4-Bromo-N-[3-(4-phenyl-1H-imidazol-1-yl)propyl]benzamide

A mixture of 28.8 g. of 4-phenyl imidazole and 25 ml. of acrylonitrile was heated at reflux temperature for 6 hours and then concentrated to remove the volatile material. The residue was mixed with 200 ml. of ethanol, 100 ml. of ammonium hydroxide and 6 g. of Raney Nickel catalyst and reduced in a Parr hydrogenator under hydrogen pressure until reduction was complete. The catalyst was removed by filtration and the filtrate was concentrated to remove the solvents. The residual oil was 4-phenyl-1H-imidazole-1-propanamine.

A mixture of 2.0 g. of 4-phenyl-1H-imidazole-1-propanamine, 50 ml. of methylenechloride and 10 ml. of 1N sodium hydroxide was stirred and 2.2 g. of 4-bromobenzoyl chloride was added. The mixture was stirred for eighteen hours, methylene chloride was added and the layers were separated. The organic layer was washed with water, dried over magnesium sulfate and concentrated. The residue was washed onto a filter with ether, giving the desired product, m.p. 132°-135° C.

EXAMPLE 77

4-Chloro-N-[3-(4-phenyl-1H-imidazol-1-yl)propyl]-benzamide

When 4-chlorobenzoyl chloride was substituted for the 4-bromobenzyl chloride of Example 76, There was obtained the title compound, m.p. 103°-105° C.

EXAMPLE 78

N-[3-(1H-Imidazol-1-yl)propyl]-2-phenoxyacetamide

A mixture of 2.28 g. of phenoxyacetic acid, 2.43 g. of 1,1'-carbonyldiimidazole and 50 ml. of tetrahydrofuran was stirred at room temperature for 2 hours, then 3.0 g. of 1H-imidazole-1-propanamine dihydrochloride was added. The reaction mixture was stirred for 18 hours, then heated at reflux temperature for 5 hours, 5 ml. of water was added, the mixture was heated for 30 minutes and then concentrated to remove the tetrahydrofuran. The residue was treated with methylene chloride and 50 ml. of 1N sodium hydroxide and the layers separated. The organic layer was washed with water, dried over magnesium sulfate and concentrated. The residue was washed onto a filter with ether, giving the desired product, m.p. 91°-93° C.

Following the procedure of this example and using the appropriate phenoxyacetic acid derivatives, the products of Examples 79 and 80 were obtained as set forth in Table XII below.

TABLE XII

| Ex. | Phenoxy Acetic Acid | Product | m.p.°C. |
|---|---|---|---|
| 79 | 4-chlorophenoxyacetic acid | 2-(4-chlorophenoxy)-N—[3-(1H—imidazol-1-yl)-propyl]acetamide | 116-119 |
| 80 | 2,3-dichlorophenoxyacetic acid | 2-(2,3-dichlorophenoxy)-N—[3-(1H—imidazol-1-yl)propyl]acetamide | oil |

EXAMPLE 81

4-Fluoro-N-[3-(1H-imidazol-1-yl)propyl]benzeneacetamide

A mixture of 1.54 g. of 4-fluorophenylacetic acid, 1.62 g. of 1,1'-carbonyldiimidazole and 30 ml. of tetrahydrofuran was stirred for 2 hours, then 1.98 g. of 1H-imidazole-1-propanamine dihydrochloride was added. Stirring was continued at room temperature for an additional 18 hours, then at reflux temperature for 5 hours, 5 ml. of water was added, the mixture was heated for 30 minutes and then concentrated to remove the volatile material. The residue was diluted with methylene chloride and 25 ml. of 1N sodium hydroxide and the layers separated. The organic layer was washed with water, dried over magnesium sulfate and concentrated, giving the desired product as a viscous oil.

EXAMPLE 82

N-[3-(1H-Imidazol-1-yl)propyl]-4-methylbenzeneacetamide

Following the procedure of Example 81, but using 4-methylphenylacetic acid, the desired product was obtained as an oil.

EXAMPLE 83

3-Chloro-N-[3-(1H-Imidazol-1-yl)propyl]benzeneacetamide

Following the procedure of Example 81, but using 3-chlorophenylacetic acid, the desired product may be obtained as an oil.

EXAMPLE 84

N-[3-(1H-imidazol-1-yl)propyl]diphenylacetamide

Following the procedure of Example 81, but using diphenylacetic acid, the desired product is obtained as crystals, m.p. 136°–138° C.

EXAMPLE 85

N-[3-(1H-Imidazol-1-yl)propyl]-α-oxo-benzeneacetamide

Following the procedure of Example 81, but using benzoylformic acid, the desired product was obtained as an oil.

EXAMPLE 86

N-[3-(1H-Imidazol-1-yl)propyl]-α-oxo-benzeneacetamide, fumarate

A mixture of 1.3 g. of N-[3-(1H-imidazol-1-yl)propyl]-α-oxo-benzeneacetamide, 10 ml. of ethanol and 0.6 g. of fumaric acid was warmed to solution and then diluted with ether. The resulting crystals were collected by filtration, washed with ether and dried in vacuo, giving the desired product, m.p. 95°–105° C.

Following the procedure of this example but using the indicated starting materials, the fumarate salt products of Examples 87–91 were obtained as set forth in Table XIII below.

TABLE XIII

| Ex. | Starting Material Product of Ex. | Product | m.p.°C. |
|---|---|---|---|
| 87 | 14 | N—[3-(1H—imidazol-1-yl)propyl]-4-(1,1-dimethylethyl)benzamide, fumarate | 90–95 |
| 88 | 81 | 4-fluoro-N—[3-(1H—imidazol-1-yl)propyl]benzeneacetamide, fumarate | 101–103 |
| 89 | 80 | 2-(2,3-dichlorophenoxy)-N—[3-(1H—imidazol-1-yl)propyl]acetamide, fumarate | 99–102 |
| 90 | 82 | N—[3-(1H—imidazol-1- | 79–81 |

TABLE XIII-continued

| Ex. | Starting Material Product of Ex. | Product | m.p.°C. |
|---|---|---|---|
|  |  | yl)propyl]-4-methyl-benzeneacetamide, hemi-fumarate |  |
| 91 | 83 | 3-chloro-N—[3-(1H—imidazol-1-yl)propyl]benzeneacetamide, fumarate | 109–111 |

EXAMPLE 92

N-[3-(1H-Imidazol-1-yl)propyl]cinnamamide

A mixture of 2.22 g. of trans-cinnamic acid, 2.43 g, of 1,1′-carbonyldiimidazole and 50 ml. of tetrahydrofuran was stirred for 2 hours, then 1.7 ml. of 1H-imidazole-1-propanamine was added. The reaction mixture was stirred for 18 hours, then 5 ml. of water was added, the mixture was heated for 30 minutes and then concentrated. Methylene chloride and 10 ml. of 1N sodium hydroxide were added and then layers were separated. The organic layer was washed with water, dried over magnesium sulfate and concentrated, giving the desired product as a viscous oil.

Following the procedure of this example but using the appropriate cinnamic acid, the products of Example 93–95 were obtained, as set forth in Table XIV below.

TABLE XIV

| Ex. | Cinnamic Acid | Product | m.p.°C. |
|---|---|---|---|
| 93 | 3-chloro-cinnamic acid | 3-chloro-N—[3-(1H—imidazol-1-yl)propyl]cinnamamide | 99–101 |
| 94 | 3,4-dichloro-cinnamic acid | 3,4-dichloro-N—[3-(1H—imidazol-1-yl)propyl]-cinnamamide | 122–124 |
| 95 | 4-chloro-cinnamic acid | 4-chloro-N—[3-(1H—imidazol-1-yl)propyl]cinnamamide | 151–153 |

EXAMPLE 96

3-Amino-N-[3-(1H-imidazol-1-yl)propyl]benzamide

A mixture of 2.35 g. of N-[3-(1H-imidazol-1-yl)propyl]-3-nitrobenzamide, 0.5 g. of 10% palladium on carbon catalyst and 150 ml. of ethanol was shaken under 45 lbs. of hydrogen in a Parr hydrogenator until the reaction was complete. The catalyst was removed by filtration and the mother liquor concentrated. The crystalline residue was washed onto a filter with ether, giving the desired product, m.p. 88°–90° C.

EXAMPLE 97

2-Amino-N-[3-(1H-imidazol-1-yl)propyl]benzamide

A mixture of 2.5 ml. of 1H-imidazole-1-propanamine, 3.2 g. of isatoic anhydride, and 30 ml. of toluene was heated at 90°–100° C. for 45 minutes and cooled. The precipitate which separated was collected by filtration. The desired product melted at 107°–110° C.

Following the procedure of this example and using the appropriate isatoic anhydrides, the products of Examples 98–103, found in Table XV, were obtained.

TABLE XV

| Ex. | Isatoic Anhydride | Product | m.p.°C. |
|---|---|---|---|
| 98 | N—methyl-isatoic anhydride | N—[3-(1H—imidazol-1-yl)propyl]-2-methyl-aminobenzamide | 140–143 |

TABLE XV-continued

| Ex. | Isatoic Anhydride | Product | m.p.°C. |
|---|---|---|---|
| 99 | N—ethyl-isatoic anhydride | 2-ethylamino-N—[3-(1H—imidazol-1-yl)propyl]benzamide | 115–117 |
| 100 | N—benzyl-isatoic anhydride | 2-benzylamino-N—[3-(1H—imidazol-1-yl)propyl]benzamide | oil |
| 101 | 5-chloro-isatoic anhydride | 2-amino-5-chloro-N—[3-(1H—imidazol-1-yl)-propyl]benzamide | 155–157 |
| 102 | N—allyl-5-chloro-isatoic anhydride | 2-Allylamino-5-chloro-N—[3-(1H—imidazol-1-yl)propyl]benzamide | 102–104 |
| 103 | 5-chloro-7-methyl-isatoic anhydride | 2-amino-5-chloro-3-methyl-N—[3-(1H—imidazol-1-yl)propyl]-benzamide dihydrochloride salt | 233–236 |

EXAMPLE 104

N-[3-(1H-imidazol-1-yl)propyl]benzenepropanamide

A mixture of 1.50 g. of 3-phenylpropionic acid, 1.62 g. of 1,1'-carbonyldiimidazole, and 40 ml. of tetrahydrofuran was stirred for 3 hours and 2.0 g. of 1H-imidazole-1-propanamine was added. The mixture was stirred for 18 hours, 5 ml. of water was added, and the reaction mixture was heated at reflux temperature for 30 minutes. The mixture was concentrated and 10 ml. 1N sodium hydroxide and 100 ml. of methylene chloride were added. The layers were separated and the organic layer was washed with water, dried over magnesium sulfate, and concentrated. The desired product was obtained as an oil, which was converted to the fumarate salt, m.p. 90°–92° C.

Following the procedure of this example and using the appropriate acids, the products of Examples 105–110, found in Table XVI, were obtained.

TABLE XVI

| Ex. | Acid | Product | m.p.°C. |
|---|---|---|---|
| 105 | 4-phenylbutyric acid | N—[3-(1H—imidazol-1-yl)propyl]benzene-butanamide | oil |
| 106 | 3-phenylbutyric acid | N—[3-(1H—imidazol-1-yl)propyl]-beta-methyl-benzenepropanamide | oil |
| 107 | 2-phenylbutyric acid | alpha-ethyl-N—[3-(1H—imidazol-1-yl)propyl]-benzeneacetamide | oil |
| 108 | 1-phenyl-1-cyclopropane carboxylic acid | 1-phenyl-N—[3-(1H—imidazol-1-yl)-propyl] cyclopropane carboxamide | oil |
| 109 | trans-2-phenyl-propane-1-carboxylic acid | 2-phenyl-N—[3-(1H—imidazol-1-yl)-propyl] cyclopropane carboxamide | oil |
| 110 | 2-phenylcylcopentane acetic acid | 2-cyclopentyl-N—[3-(1H—imidazol-1-yl)propyl] benzeneacetamide | oil |

EXAMPLE 111

N-Benzyl-N-[3-(1H-imidazol-1-yl)propyl]benzamide

A mixture of 4.58 g. of N-[3-(1H-imidazol-1-yl)propyl]benzamide, 40 ml. of dimethylformamide, and 0.96 g. of 50% sodium hydride in oil was stirred for 2 hours and 2.62 g. of benzyl bromide was added. The mixture was stirred for 24 hours, concentrated to remove the dimethyl formamide, diluted with water and methylene chloride, and the layers separated. The organic layer was washed with water, dried over magnesium sulfate, and concentrated. The oil was twice washed with hexane and again concentrated. The desired product was obtained as an oil.

EXAMPLE 112

N-Ethyl-N-[3-(1H-imidazol-1-yl)propyl]benzamide

The above compound is obtained when ethyl bromide is substituted for benzyl bromide in the procedure of Example 111.

EXAMPLE 113

3-(1H-Imidazol-1-yl)-2-methylpropanamine

A mixture of 15.0 g. of imidazole and 25 ml. of methacrylonitrile was heated at reflux temperature for 18 hours and then concentrated to remove the volatile material. The residue was mixed with 150 ml. of ethanol, 75 ml. of ammonium hydroxide and 6 g. of Raney Nickel catalyst and reduced in a Parr hydrogenator under hydrogen pressure until reduction was complete. The catalyst was removed by filtration and the mother liquor was concentrated to remove the solvents. The residual oil was used in reactions without further purification.

EXAMPLES 114–117

Substituted N-[3-(1H-imidazol-1-yl)-2-methylpropyl]benzamides

By reaction with the benzoyl chlorides in Table XVII by the procedure of Example 27, the products of Table XVII below were obtained.

TABLE XVII

| Ex. | Benzoyl Chloride | Product | m.p.°C. |
|---|---|---|---|
| 114 | 4-chlorobenzoyl chloride | 4-chloro-N—[3-(1H—imidazol-1-yl)-2-methylpropyl]benzamide fumarate | 141–144 |
| 115 | 3-chlorobenzoyl chloride | 3-chloro-N—[3-(1H—imidazol-1-yl)-2-methylpropyl]benzamide | glass |
| 116 | 3,4-dichlorobenzoyl chloride | 3,4-dichloro-N—[3-(1H—imidazol-1-yl)-2-methylpropyl]benzamide | glass |
| 117 | 4-bromobenzoyl | 4-bromo-N—[3-(1H—imidazol-1-yl)-2-methylpropyl]benzamide | 141–144 |

EXAMPLES 118–121

3-(1H-Imidazol-1-yl)butanamine

When crotononitrile is reacted with imidazole by the procedure of Example 113, 3-(1H-imidazol-1-yl)butanamine is obtained as an oil. By reaction of this diamine with the appropriate benzoyl chloride by the procedure of Example 27, the products set forth in Table XVIII below are obtained.

TABLE XVIII

| Ex. | Benzoyl chloride | Product | m.p.°C. |
|---|---|---|---|
| 118 | 3-chlorobenzoyl chloride | 3-chloro-N—[3-(1H—imidazol-1-yl)-butyl]benzamide | 107–109 |
| 119 | 3,4-dichlorobenzoyl chloride | 3,4-dichloro-N—[3-(1H—imidazol-1-yl)-butyl]benzamide | 159–161 |
| 120 | 4-bromobenzoyl | 4-bromo-N—[3-(1H— | 122–124 |

TABLE XVIII-continued

| Ex. | Benzoyl chloride | Product | m.p.°C. |
|---|---|---|---|
|  | chloride | imidazol-1-yl)-butyl]benzamide |  |
| 121 | 4-chlorobenzoyl chloride | 4-chloro-N—[3-(1H—imidazol-1-yl)-butyl]benzamide | 102–104 |

EXAMPLE 122

3-(1H-Imidazol-1-yl)-3-phenylpropanamine

A solution of 6.0 g. of 3-(1H-imidazol-1-yl)propiophenone in 100 ml. of methanol was stirred as 23.1 g. of ammonium acetate, and then 1.35 g. of sodium cyanoborohydrate was added. After 6 days at room temperature, 60 ml. of concentrated hydrochloric acid was added and the solvent was distilled off. The residue was treated with 65 ml. of 10N sodium hydroxide, 25 g. of sodium chloride and 200 ml. of methylene chloride and the layers were separated. The organic layer was washed with water, dried over magnesium sulfate, and concentrated to obtain the desired product as a viscous oil, 5.4 g. When this was reacted with 4-chlorobenzoyl chloride and 4-bromobenzoyl chloride by the procedure of Example 27, the compounds set forth in Table XIX were obtained.

TABLE XIX

| Ex. | Compounds | m.p.°C. |
|---|---|---|
| 123 | 4-chloro-N—[3-(1H—imidazol-1-yl)-1-phenylpropyl]benzamide | 160–162 |
| 124 | 4-bromo-N—[3-(1H—imidazol-1-yl)-1-phenylpropyl]benzamide | 158–163 |

EXAMPLE 125

N-[3-(1H-imidazol-1-yl)propyl]phthalamic acid

A mixture of 0.01 mole of phthalic anhydride, 0.01 mole of 3-(1H-imidazol-1-yl)propanamine and 30 ml. of methylene chloride was stirred at room temperature for 3 hours and concentrated. The residue was recrystallized from ethanol whereby the desired product, m.p. 160°–162° C., was obtained. By substituting 3-fluorophthalic anhydride, 4,5-dichlorophthalic anhydride, and 4-methylphthalic anhydride for the phthalic anhydride of this example, the compounds set forth in Table XX below were obtained.

TABLE XX

| Ex. | Compounds | m.p.°C. |
|---|---|---|
| 126 | 3-fluoro-N—[3-(1H—imidazol-1-yl)propyl]phthalamic acid | 160–162 |
| 127 | 4-methyl-N—[3-(1H—imidazol-1-yl)propyl]phthalamic acid | 161–163 |
| 128 | 4,5-dichloro-N—[3-(1H—imidazol-1-yl)propyl]phthalamic acid | 176–178 |

EXAMPLE 129

2-[4-(1H-imidazol-1-yl)butyl]-1H-isoindole-1,3(2H)-dione

A mixture of 0.01 mole of phthalic anhydride and 0.01 mole of 1H-imidazol-1-butanamine was heated in an oil bath at 160° C. for one hour. The reaction mixture was cooled and the product was purified by HPLC using ethyl acetate and a silica gel column. The melting point was 75°–77° C.

When 4-bromophthalic anhydride was reacted with the appropriate amine by the procedure of Example 129, the following compounds were obtained.

TABLE XXI

| Ex. | Compounds | m.p.°C. |
|---|---|---|
| 130 | 4-bromo-2-[3-(1H—imidazol-1-yl)propyl]-1H—isoindole-1,3(2H)—dione | oil |
| 131 | 4-bromo-2-[4-(1H—imidazol-1-yl)butyl]-1H—isoindole-1,3(2H)—dione | 110–112 |
| 132 | 4-bromo-2-[3-(1H—imidazol-1-yl)butyl]-1H—isoindole-1 3(2H)—dione | oil |
| 133 | 4-bromo-2-[5-(1H—imidazol-1-yl)pentyl]-1H—isoindole-1,3(2H)—dione | 102–104 |

EXAMPLES 134–135

Substituted 2-[4-(1H-imidazol-1-yl)butyl]-1H-isoindole-1,3(2H)-diones

By reacting 1H-imidazol-1-butanamine with other phthalic anhydride derivatives by the procedure of Example 129, the following compounds were obtained.

TABLE XXII

| Ex. | Compounds | m.p.°C. |
|---|---|---|
| 134 | 4-chloro-2-[4-(1H—imidazol-1-yl)butyl]-1H—isoindole-1,3(2H)—dione | 80–83 |
| 135 | 4,5-dichloro-2-[4-(1H—imidazol-1-yl)butyl]-1H—isoindole-1,3(2H)—dione | 105–108 |

EXAMPLES 136–139

Substituted 2-[3-(1H-imidazol-1-yl)propyl]-1H-isoindole-1,3(2H)-diones

By reacting 1H-imidazle-1-propanamine with substituted phthalic anhydrides by the procedure of Example 129, the following compounds were obtained.

TABLE XXII

| Ex. | Compound | m.p. °C. |
|---|---|---|
| 136 | 4-methyl-2-[3-(1H—imidazol-1-yl)propyl]-1H—isoindole-1,3(2H)—dione | 83–85 |
| 137 | 4-nitro-2-[3-(1H—imidazol-1-yl)propyl]-1H—isoindole-1,3(2H)—dione | 141–143 |
| 138 | 4,5-dichloro-2-[3-(1H—imidazol-1-yl)propyl]-1H—isoindole-1,3(2H)—dione | 145–152 |
| 139 | 3-chloro-2-[3-(1H—imidazol-1-yl)propyl]-1H—isoindole-1,3(2H)—dione | 92–94 |

EXAMPLE 140

4-Amino-2-[3-(1H-imidazol-1-yl)propyl]-1H-isoindole-1,3(2H)-dione

A mixture of 0.1 mole of 4-nitro-2-[3-(1H-imidazol-1-yl)propyl]-1H-isoindole-1,3(2H)-dione, 200 ml. of ethanol, 0.1 mole of 12N hydrochloric acid and 1.0 g. of Pd/C catalyst was reduced in a Parr hydrogenator under an initial $H_2$ pressure of 45 pounds per square inch pressure. The catalyst was filtered off and the solvent was removed to obtain the desired compound as the hydrochloride salt.

EXAMPLE 141

2-[4-(1H-imidazol-1-yl)butyl]-1H-isoindole-1,3(2H)-dione

A mixture of 0.1 mole of 2-(4-bromobutyl)-1H-isoindole-1,3(2H)-dione and 0.1 mole of the silver salt of imidazole were heated in 300 ml. of dimethylformamide for 8 hours. The reaction mixture was concentrated to remove the solvent and the residue was boiled with 200 ml. of toluene and filtered to remove the insoluble material. The toluene layer was concentrated and the desired product was purified by HPLC using ethyl acetate and a silica gel column.

EXAMPLE 142

2-[4-(1H-imidazol-1-yl)butyl]-1H-isoindole-1,3(2H)-dione

A mixture of 0.01 mole of phthalimide and 0.01 mole of 1H-imidazol-1-butanamine was heated in an oil bath at 140° for 1 hour. The reaction mixture was cooled to obtain the desired product.

EXAMPLE 143

2-[4-(1H-imidazol-1-yl)butyl]-1H-isoindole-1,3(2H)-dione

A mixture of 0.02 mole of potassium phthalimide, 0.01 mole of N-(4-bromobutyl)imidazole hydrobromide and 100 ml. of dimethyl formamide was gradually heated to 80° C. and held at this temperature for 3 hours. The solvent was removed in vacuo and the residue was purified by HPLC using ethyl acetate and a silica gel column.

EXAMPLE 144

4-Chloro-N-[4-(1H-imidazol-1-yl)-2-butynyl]benzamide

A mixture of 27.8 g. of N-(4-bromo-2-butynyl)phthalimide, 9.0 g. of sodium imidazole and 150 ml. of dimethylformamide is heated at 80° C. for 3 hours and then concentrated to remove the solvent. The residue is extracted with 500 ml. of hot toluene and the toluene layer is concentrated to a viscous oil which is further purified by HPLC, developed with ethyl acetate to obtain 2-[4-(1H-imidazol-1-yl)-2-butynyl)]-1H-isoindole-1,3(2H)-dione, m.p. 139°-141° C.

A mixture of 0.05 mole of 2-[4-(1H-imidazol-1-yl)-2-butynyl)]-1H-isoindole-1,3(2H)-dione, 0.05 mole of hydrazine hydrate and 100 ml. of ethanol was heated on a steam bath for 3 hours and then treated with 100 ml. of 3N hydrochloric acid and heated at reflux temperature for an additional 2 hours. The insoluble material was filtered off and the mother liquor was concentrated to a low volume and again filtered. The remainder of the volatile material was distilled off and the residue was treated with saturated potassium carbonate solution. The 4-(1H-imidazol-1-yl)-butynamine was extracted into methylene chloride and isolated as an oil by concentration of this solution.

A mixture of 2.68 g. of 4-(1H-imidazol-1-yl)-butynamine, 20 ml. of 1N sodium hydroxide and 75 ml. of methylene chloride was stirred and 2.6 ml. of 4-chlorobenzoyl chloride was added. The mixture was stirred for 18 hours, 5 ml. of 1N sodium hydroxide was added and the layers were separated. The organic layer was washed with water, dried over magnesium sulfate and concentrated to obtain the desired compound.

EXAMPLE 145

4,5-Dichloro-2-[3-(4-methyl-1H-imidazol-1-yl)propyl]-1H-isoindole-1,3(2H)-dione

A mixture of 4.34 g. of 4,5-dichlorophthalic anhydride and 2.78 g. of 3-(4-methyl-1H-imidazol-1-yl)propanamine was heated in an oil bath at 165° C. for 40 minutes. The mixture was then boiled with 100 ml. toluene and the toluene layer was allowed to cool to room temperature and then filtered from the insoluble material. The toluene layer was concentrated to remove the solvent and the crystalline residue was recrystalized from ethyl acetate to obtain the desired compound, m.p. 147°-151° C.

EXAMPLE 146

4-Chloro-N-[4-(1H-imidazol-1-yl)-2-butenyl]-benzamide carboxamide

A mixture of 100 g. of 1.4-dichlorobutene, 74 g. of potassium phthalimide and 1500 ml. of dimethylformamide was stirred at room temperature for 24 hours. The reaction mixture was concentrated to remove the solvent and residue taken up with 2000 ml. of boiling hexane and again concentrated. The residue was dissolved in methylene chloride, washed with water, dried over magnesium sulfate and concentrated to obtain 46 g. of N-(4-chloro-2-butenyl)isoindole-1,3(2H)-dione, m.p. 79°-81° C.

A mixture of 23.5 g. of N-(4-chloro-2-butenyl)-isoindole-1,3(2H)-dione, 11.0 g. of sodium imidazol and 200 ml. of dimethyl formamide was heated on the steam bath for 18 hours and concentrated to remove the solvent; the residue was taken up in methylene chloride, washed with water, dried with magnesium sulfate and again concentrated. The residue was dissolved in hot ethylacetate and allowed to cool and N-[4-(1H-imidazol-1-yl)-2-butenyl]isoindole-1,3-(2H)-dione, m.p. 106°-108° C., was obtained.

A mixture of 26.8 g. of N-[4-(1H-imidazol-1-yl)-2-butenyl]isoindole-1,3-(2H)-dione, 4.85 ml of hydrazine hydrate and 250 ml. of ethanol was heated at reflux temperature for 6 hours. The mixture was cooled and 225 ml. of 3N hydrochloric acid was added and the mixture was again heated at reflux temperature for 3 hours. The precipitate was filtered off and the mother liquor was concentrated once more and then treated with saturated potassium carbonate solution. Extraction with methylene chloride resulted in 4-(1H-imidizol-1-yl)-2-butenamine, obtained as an oil.

A solution of 1.65 g. of 4-(1H-imidazol-1-yl)-2-butenamine, 60 ml. of methylene chloride and 12 ml. of 1N sodium hydroxide was stirred and 1.6 ml. of 4-chlorobenzoylchloride was added. The reaction mixture was stirred for 18 hours, 40 ml. of methylene chloride and 5 ml. of 1N sodium hydroxide was added and the layers were separated. The organic layer was washed with water, dried over magnesium sulfate and concentrated and the desired compound was obtained, m.p. 124°-126° C.

We claim:

1. A compound selected from the group consisting of those of the formula:

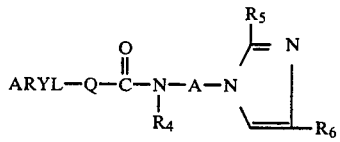

wherein A is a divalent moiety of the formulae:

$-C_nH_{2n}-$, $-CH_2CH=CHCH_2-$, $-CH_2C\equiv CCH_2-$ or 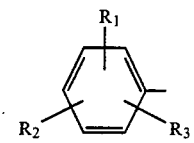

wherein n is an integer from 2 to 8, inclusive, ARYL is 1-naphthyl, 2-naphthyl, diphenylmethyl, 9-fluorenyl or a moiety of the formula:

(structure with $R_1$, $R_2$, $R_3$)

wherein $R_1$, $R_2$ and $R_3$ are each hydrogen, halogen, trifluoromethyl, cyano, carboxy, amino, alkyl($C_1$–$C_4$), alkoxy($C_1$–$C_4$), benzylamino, allylamino, alkyl($C_1$–$C_3$)amino, dialkyl($C_1$–$C_3$)amino, alkyl($C_1$–$C_3$)thio, alkyl($C_1$–$C_3$)sulfonyl, acetyl, acetylamino, phenyl or benzoyl, Q is a divalent moiety of the formulae:

$-CH=CH-$, $-O-CH_2-$, $-\overset{O}{\underset{\|}{C}}-$, $-C_mH_{2m}-$,

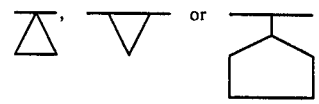

wherein m is zero, 1, 2 or 3, $R_4$ is hydrogen, alkyl($C_1$–$C_3$) or benzyl, and $R_5$ and $R_6$ are each hydrogen, alkyl($C_1$–$C_3$) or phenyl; and the pharmacologically acceptable acid-addition salts thereof.

2. The compound according to claim 1; 4-chloro-N-[3-(1H-imidazol-1-yl)propyl]benzamide.

3. The compound according to claim 1; 3-chloro-N-[3-(1H-imidazol-1-yl)propyl]benzamide.

4. The compound according to claim 1; 4-bromo-N-[3-(1H-imidazol-1-yl)propyl]benzamide.

5. The compound according to claim 1; 3,4-di-chloro-N-[4-(1H-imidazol-1-yl)butyl]benzamide.

6. The compound according to claim 1; 4-bromo-N-[3-(4-methyl-1H-imidazol-1-yl)propyl]benzamide.

7. The compound according to claim 1; 4-chloro-N-[3-(2-methyl-1H-imidazol-1-yl)propyl]benzamide.

8. The compound according to claim 1; 3-chloro-N-[3-(4-methyl-1H-imidazol-1-yl)propyl]benzamide.

9. The compound according to claim 1; 4-chloro-N-[3-(2-methyl-1H-imidazol-1-yl)propyl]benzamide.

10. The compound according to claim 1; 3,4-dichloro-N-[3-(4-methyl-1H-imidazol-1-yl)propyl]benzamide.

11. The compound according to claim 1; 4-trifluoromethyl-N-[3-(4-methyl-1H-imidazol-1-yl)propyl]benzamide.

12. The compound according to claim 1; 4-trifluoromethyl-N-[4-(1H-imidazol-1-yl)butyl]benzamide.

13. The compound according to claim 1; N-[3-(1H-imidazol-1-yl)propyl]-4-methylbenzeneacetamide hemifumarate.

14. The compound according to claim 1; 4-Bromo-N-[3-(2-phenyl-1H-imidazol-1-yl)propyl]benzamide fumarate.

15. A thromboxane synthetase enzyme inhibiting composition of matter in dosage unit form comprising from about 10 mg. to about 700 mg. of a compound of claim 1 in association with a pharmaceutical carrier.

* * * * *